US009216234B2

(12) United States Patent
Bianco-Peled et al.

(10) Patent No.: US 9,216,234 B2
(45) Date of Patent: Dec. 22, 2015

(54) SEALANTS, MANUFACTURING THEREOF, AND APPLICATION THEREOF

(75) Inventors: Havazelet Bianco-Peled, Tivon (IL); Ohad Kimhi, Kiryat Yam (IL)

(73) Assignee: Technion Research & Development Foundation Ltd., Haifa (IL)

( * ) Notice: Subject to any disclaimer, the term of this patent is extended or adjusted under 35 U.S.C. 154(b) by 682 days.

(21) Appl. No.: 13/375,708

(22) PCT Filed: Jun. 1, 2010

(86) PCT No.: PCT/IL2010/000431
§ 371 (c)(1),
(2), (4) Date: Feb. 13, 2012

(87) PCT Pub. No.: WO2010/140146
PCT Pub. Date: Dec. 9, 2010

(65) Prior Publication Data
US 2012/0132105 A1    May 31, 2012

Related U.S. Application Data

(60) Provisional application No. 61/182,771, filed on Jun. 1, 2009.

(51) Int. Cl.
*A61L 15/00*      (2006.01)
*A61L 17/00*      (2006.01)
*A61L 24/00*      (2006.01)
*A61L 24/08*      (2006.01)

(52) U.S. Cl.
CPC ......... *A61L 24/0015* (2013.01); *A61L 24/0031* (2013.01); *A61L 24/0042* (2013.01); *A61L 24/08* (2013.01); *A61L 2300/252* (2013.01); *A61L 2300/414* (2013.01); *A61L 2300/416* (2013.01); *A61L 2300/43* (2013.01)

(58) Field of Classification Search
USPC ........................................................ 606/212
See application file for complete search history.

(56) References Cited

U.S. PATENT DOCUMENTS

| 705,219 | A | 7/1902 | Dempster et al. |
|---|---|---|---|
| 2,884,389 | A | 4/1959 | Corwin et al. |
| 3,802,897 | A | 4/1974 | Voigt et al. |
| 4,057,588 | A | 11/1977 | Zengel et al. |
| 5,520,727 | A | 5/1996 | Vreeland et al. |
| 5,804,213 | A | 9/1998 | Rolf |
| 6,146,497 | A | 11/2000 | Nguyen |
| 6,193,994 | B1 | 2/2001 | Lee et al. |
| 6,544,503 | B1 | 4/2003 | Vanderhoff et al. |
| 6,638,917 | B1 | 10/2003 | Li et al. |
| 7,365,190 | B2 | 4/2008 | Couture et al. |
| 8,673,354 | B2 | 3/2014 | Bianco-Peled et al. |
| 2002/0010150 | A1 | 1/2002 | Cortese et al. |
| 2002/0086175 | A1 | 7/2002 | Parg et al. |
| 2004/0018241 | A1 | 1/2004 | Houze et al. |
| 2006/0269480 | A1 | 11/2006 | Amir et al. |
| 2008/0020026 | A1 | 1/2008 | Cochrum et al. |
| 2008/0295735 | A1 | 12/2008 | Ragaru et al. |
| 2012/0132105 | A1* | 5/2012 | Bianco-Peled et al. .... 106/162.9 |

FOREIGN PATENT DOCUMENTS

| EP | 1607412 A1 | 12/2005 |
|---|---|---|
| FR | 804128 | 10/1936 |
| GB | 2336156 | 10/1999 |
| GB | 2408207 | 5/2005 |
| JP | 2145505 | * 5/1990 |
| JP | 2145505 A | 6/1990 |
| JP | 2002509171 | 3/2002 |
| WO | 9741900 | 11/1997 |
| WO | 0102478 | 1/2001 |
| WO | 03008003 | 1/2003 |
| WO | 2006/092798 | 9/2006 |
| WO | WO 2007066837 A1 | 6/2007 |
| WO | 2007103209 | 9/2007 |
| WO | 2009/060438 | 5/2009 |
| WO | 2009060439 | 5/2009 |

OTHER PUBLICATIONS

Bitton, R., "Phloroglucinol-based biomimetic adhesives for medical applications", Acta Biomater. Jun. 2009; 5(5):1582-7. doi: 10.1016/j.actbio.2008.10.004. Epub Oct. 22, 2008.
Berglin et al; "Enzymatic Cross-Linking of A Phenolic Polymer Extracted From the Marine Alga Fucus Serratus", Biomacromolecules, 5: 2376-2383, 2004.
Draget et al: "Alginate-based solid media for plant tissue culture", Appl. Microbiol. Biotechnol, 31:79-83 (1989).
Dumitriu: "Polysaccharides as Biomaterials", Polymeric Biomaterials, Chap.1: 1-61, 2002.
Ennker et al: "Formaldehyde-Free Collagen Glue in Experimental Lung Gluing", Annals of Thoracic Surgeons, 57: 1622-1627, 1994.
Huang et al: "Synthesis and Characterization of Self-Assembling Block Copolymers Containing Adhesive Moieties", Polymer Preprints, 42(2): 147-148, 2001.
Ishihara et al: "Photocrosslinkable Chitosan: An Effectice Adhesive With Surgical Applications", International Congress Series, 1223: 251-257, 2001.
Ismail et al: "Phloroglucinol: Novel Synthesis and Role of the Magnesium Cation on Its Binding With Human Serum Albumin (HSA) Using a Biochromatographic Approach Based on Langmuir Isotherms", Journal of Pharmaceutical and Biomedical Analysis, 32: 549-553, 2003.

(Continued)

*Primary Examiner* — Melvin C Mayes
*Assistant Examiner* — Colette Nguyen
(74) *Attorney, Agent, or Firm* — Roach Brown McCarthy & Gruber, P.C.; Kevin D. McCarthy

(57) ABSTRACT

Method comprising: applying uncured pre-gel (UP) to surface; contacting UP with cross-linking agents; allowing applied UP to cure, increasingly adhere to first surface, source of agents: solid support comprising agent, or insoluble agent salt in UP, wherein trigger compound is added to UP, or spraying/coating agent, with solid support added.

22 Claims, 4 Drawing Sheets

(56) References Cited

OTHER PUBLICATIONS

Lee et al: "Synthesis and Gelation of DOPA-Modified Poly(Ethylene Glycol) Hydrogels", Biomacromolecules, 3: 1038-1047, 2002.

Li et al: "Novel Visible-Light-Induced Photocurable Tissue Adhesive Composed of Multiply Styrene-Derivatized Gelatin and Poly(Ethylene Glycol) Diacrylate", Journal of Biomedical Materials Research Part B: Applied Biomaterials, 66B: 439-446, 2003.

Lipatova et al: "Medical Polymer Adhesives", Advances in Polymer Science, 79: 65-93, 1986.

Lucas et al: "Extra-Organismic Adhesive Proteins", Biopolymers, 8: 359-382, 2001.

Manabe et al: "In Situ-Formed, Tissue-Adhesive Co-Gel Composed of Styrenated Gelatin and Styrenated Antibody: Potential Use for Local Anti-Cytokine Antibody Therapy on Surgically Resected Tisues", Biomaterials, 25: 5867-5873, 2004.

Masuda et al: "Photocured, Styrenated Gelatin-Based Microspheres for De Novo Adipogenesis Through Corelase of Basic Fibroblast Growth Factor, Insulin, and Insulin-Like Growth Factor I", Tissue Engineering, 10 (3/4): 523-536, 2004.

McDermott et al: "Mechanical Properties of Biomimetic Tissue Ashesive Based on the Microbial Transglutaminase-Catalyzed Crosslinking of Gelatin", Biomacromolecules, 5: 1270-1279, 2004.

Mo et al: "Soft Tissue Adhesive Composed of Modified Gelatin and Polysaccharides", Journal of Biomaterials Science, Polymer Edition, 11(4): 341-351, 2000.

Reece et al: "A Prospectus on Tissue Adhesives", The American Journal of Surgery, 182: 40S-44S, 2001.

Singer et al: "A Review of the Literature on Octylcyanoacrylate Tissue Adhesive", The American Journal of Surgery, 187: 238-248, 2004.

Vreeland et al: "Polyphenols and Oxidases in Substratum Adhesion by Marine Algae and Mussels", Journal of Phycology, 34: 1-8, 1998.

Waite: "Nature's Underwater Adhesive Specialist", International Journal of Adhesion and Adhesives, 7(1): 9-14, Jan. 1987.

Webster et al: "Adhesives for Medical Applications", Polymeric Biomaterials, Chap.26: 703-737, 2002.

White et al: "The Use of a Novel Tissue Sealant as a Hemostatic Adjunct in Cardiac Surgery", Heart Surgery Forum, 3(1): 56-61, 2000.

Yamamoto et al: "Synthesis and Wettability Characteristics of Model Adhesive Protein Sequences Inspired by a Marine Mussel", Biomacromolecules, 1: 543-551, 2000.

Yu et al: "Synthetic Polypeptide Mimics of Marine Adhesives", Macromolecules, 31: 4739-4745, 1998.

Shiro et al. "Presence of endogenous calcium ion and its functional and structural regulation in horseradish peroxidase." J Biol Chem. Jul. 15, 1986;261(20):9382-90.

* cited by examiner

SEALANTS, MANUFACTURING THEREOF, AND APPLICATION THEREOF

FIELD OF THE INVENTION

The present invention relates to adhesives, sealants and methods of applying the same. More particularly, the present invention relates to materials and methods that can be used to produce an adhesive or sealant. The method of the present invention can optionally be used to produce an adhesion-barrier.

BACKGROUND OF THE INVENTION

A common difficulty associated with surgical procedures is extensive bleeding or leaks of other bodily fluids and gases, resulting, for example, from incomplete tissue reattachment. Surgical adhesives can be used to help reattach tissues and to help seal tissue injuries, and thus to control the extent of undesired leaks. For example, tissue adhesives can be used as sealants to minimize blood loss, by applying them on injured blood vessels.

However, many currently available surgical adhesives and sealants still suffer from serious drawbacks.

Some of the synthetic adhesives used have low biocompatibility, low adherence to wet surfaces and potential toxicity, and others have low mechanical strength, tendency to swell and are costly.

Biological adhesives such as fibrin adhesives show poor mechanical tissue-bonding properties, their adherence to wet surfaces is limited, and they are potentially immunogenic, as they are based on proteins.

Another common complication associated with surgical procedures is postoperative adhesion, i.e. unwanted tissue growths occurring between layers of adjacent tissues or between tissues and internal organs. Adhesions are often induced by the healing process, and when present might cause numerous postsurgical complications, including patient's pain, functional obstruction, and sometimes difficult reoperation.

To solve these problems, physical barriers have been used to isolate the traumatized tissue from surrounding organs. Various natural and synthetic polymer films, membranes, and nonwoven fabrics have been developed as nonabsorbable or absorbable physical barrier materials. These barriers are reported to be effective in reducing postoperative adhesions, however they have limitations including difficulty in handling for their lack of flexibility, loose contact with applied tissue, and need for sutural fixation because of their sheet-like form.

Materials such as carbohydrates and in particular alginates may be formed into layers and films that may be useful as biocompatible substrates, for use as surgical devices. However, such compositions are not considered to have adhesive properties, and are commonly used externally as wound dressings or internally as adhesion-barriers.

For example, U.S. Pat. No. 6,638,917 to SCIMED LIFE SYSTEMS, INC. [US] describes devices for insertion into a body to reduce adhesion, which has an adhesion-barrier, the device including ionically cross-linked alginate.

Some of the devices according to U.S. Pat. No. 6,638,917 are described to additionally have strengthening fillers, which are added to alginate which is cross linked outside the body. Therefore, while augmenting the mechanical strength of the device. These devices require suturing, which might be damaging to the tissue.

PCT/GB1997/001244 to: ADVANCED MEDICAL SOLUTIONS [GB] relates to a hydrogel product that comprises coherent fibrous structure impregnated with an aqueous solution of a hydrogel precursor material, said fibres incorporating cations which are capable of cross-linking said precursor material to form a fibre reinforced hydrogel as the hydrogel product.

Similarly, EP1607412 to First Water Ltd. [GB] describes a hydrogel/fibre composite that includes fibres of a fibrous material impregnated with a precursor solution comprising at least one polymerisable, and optionally also cross linkable, monomer such that at least partial swelling of the fibres takes place; and polymerizing, and optionally also cross-linking, the at least one monomer after impregnation the cross-linking not initiated solely by cation release from the fibres of the fibrous material.

Both PCT/GB1997/001244 and EP1607412 describe wound dressings in the form of a hydrogel, which is non-adhesive, and intended for external use to support wound healing.

U.S. Pat. No. 5,804,213 to LECTEC CORPORATION [US] relates to a prepackaged wound dressing including dry particulate solids that are dispersed in a liquid and then applied to a wound, the solids forming a gel. The actual dispersion is performed before application.

JP 2145505 to KOKEN KK [JP] describes a removable sheet pack for application to skin that includes a support, e.g. nonwoven fabric, crosslinkable gel (alginic acid and a water soluble polymer such as polyvinyl pyrrolidone, and cross linking agent, e.g. calcium chloride.

Therefore, the references cited above refer to carbohydrate compositions that include a solid support and have cross-linked layers that were created ex-situ, require employing means such as suturing to attach the compositions in-situ, or are used externally on skin.

Some water-soluble carbohydrate compositions are described to have poor adhesive properties.

For example, WO07/066,837 to LG HOUSEHOLD & HEALTH CARE LTD. [KR] describes an adhered teeth whitening film prepared in-situ, from water-soluble agents that include for example alginate and a calcium ion-source, which form together a water-insoluble film on the surface of teeth in the oral cavity through in situ gelling. However, in order to improve the adherence to teeth, an additional compound is included with one of the agents. Indeed, it is stated that a disadvantage of conventional alginate systems is poor adhesion.

Similarly, U.S. Pat. No. 6,193,994 to SAMYANG CORPORATION [KR] describes a dental composition prepared in-situ, which is stated to enable a drug to remain in a periodontal pocket for a prolonged time. The composition is said to be prepared by making a mixture of microspheres containing a drug and a water-soluble polymer such as a polysaccharide, making the mixture into the form of film or strip or/and coating the film or strip with a cation aqueous solution such as calcium or barium.

However, the longevity of the composition is due to complexation of the polymer with the cation decreasing the solubility of the composition in water and slowing the rate of swelling of the composition.

Such compositions, while perhaps suitable for uses such as dental treatment, lack mechanical strength and adherence, typically required in compositions for uses such as placement within a patient during a surgical procedure for adhesion to a tissue.

One object of the present invention is to provide simple, non-toxic, strong, strongly adhesive and economical tissue adhesives, suitable for example for sustaining internal surgical incision closure.

Another object of the present invention is to provide a physical barrier that adheres, preferably strongly and effectively, to a tissue, thereby reducing or obviating the need for sutural fixation, while still providing desired isolation from nearby organs and tissues.

For example, in those surgeries where a tissue adhesive is used as a sealant to minimize leaks, it would be beneficial if the said sealant could also function as a tissue adhesion barrier.

It is another object of the present invention to provide methods of application of the adhesive in the site that requires tissue repair, tissue sealing or other treatments. The materials and methods of application may involve the use of additional materials other than the glue.

SUMMARY OF THE INVENTION

According to one aspect of the invention, a multi component adhesive is provided, the adhesive comprising:
  a) uncured pre\-gel that comprises at least one water miscible cross-linkable polymer selected from at least one of a group comprising naturally existing form of a carbohydrate, a synthetically prepared form of carbohydrate and a salt of a polysaccharide;
  b) a biocompatible solid support comprising at least one cross linking agent or water-soluble salt thereof,
wherein the uncured pre-gel applied to a first surface is capable of curing and increasingly adhering to the surface after adding the solid support to the uncured pregel.

According to another aspect of the invention, a multi component adhesive is provided, the adhesive comprising:
  a) uncured pre-gel that comprises:
    at least one water miscible cross-linkable polymer selected from at least one of a naturally existing form of a carbohydrate, a synthetically prepared form of carbohydrate and a salt of a polysaccharide, and at least one water-insoluble salt of a cross linking agent
  b) a composition comprising at least one trigger compound capable of triggering dissolution of the salt of the cross linking agent into the pre-gel,
wherein the uncured pre-gel applied to a first surface is capable of curing and increasingly adhering to the first surface after adding the composition comprising the trigger compound to the uncured pre-gel.

In some embodiments wherein the solid support comprises the salt of the cross-linking agent, the uncured pre-gel further comprises an aqueous liquid capable of dissolving the salt.

Some of the embodiments wherein the uncured pre-gel and/or composition comprise at least one trigger compound, further comprise an aqueous liquid capable of dissolving the salt of the cross linking agent after adding the composition comprising the trigger compound to the uncured pre-gel.

In embodiments wherein solid support comprises the salt of the cross-linking agent and both the pre-gel and the solid support are dry, curing occurs upon adding an aqueous liquid capable of dissolving the salt to the solid support and/or uncured pre-gel, after adding the solid support to the uncured pre-gel.

Some embodiments, wherein both the pre-gel and the composition comprising at least one trigger compound are dry, have the curing and adhering to the first surface occur upon adding an aqueous liquid capable of dissolving the salt to the uncured pre-gel and/or composition comprising at least one trigger compound.

Preferably, the multi component adhesive further comprises a biocompatible solid support.

Most preferably, the biocompatible solid support is bioabsorbable.

The solid support is selected from one or more of a group of suitable materials, for example: poly($\alpha$-caprolactone) (PCL), poly(glycolide) (PGA), poly(lactide) (PLA), and poly(glycolide-co-lactide) (PLGA), and oxidized regenerated cellulose, and hydrophilic water-soluble polymer, selected from one or more of the group comprising;
alginate, polyethylene glycol, polyvinyl alcohol, dextran, and pectin.

The solid support may comprise a mesh, which may include a fibrous structure.

The multi component adhesive may further comprise non-soluble suspended solids, for example in the form of particles comprising fibers.

The at least one cross linking agent may comprise multi-valent charged materials made from dissolution of one or more of a group comprising polyelectrolytes, organic salts, and inorganic salts, preferably salts of divalent ions.

Some embodiments further comprise one or more therapeutic materials selected from one or more of a group comprising drugs, therapeutic proteins, growth factors, and hormones.

In particular, some embodiments include therapeutic materials selected from the group comprising: anti cancer drugs, and anti arrhythmia drugs.

The trigger compound is preferably selected from a group comprising D-gluco-d-lactone (GDL) salts and acetic acid.

For some embodiments, the cured pre-gel is capable of being an adhesion barrier to a second surface, wherein said second surface is selected from a group of tissue surface, synthetic graft surface, and organ surface.

According to another aspect of the invention, a method of in situ application of a multi component adhesive to a subject is provided, the method comprising:
applying an uncured pre-gel to a first surface within the subject, the pre-gel comprising at least one water miscible cross-linkable polymer selected from at least one of a naturally existing form of a carbohydrate, a synthetically prepared form of carbohydrate and a salt of a polysaccharide; subsequently contacting the uncured pre-gel with one or more cross linking agents;
subsequently allowing the applied uncured pre-gel to cure and increasingly adhere to the first surface, wherein the source of the cross linking agents is selected from one or more of the options comprising:
  A. a solid support comprising at least one cross linking agent or water-soluble salt thereof;
  B. a water-insoluble salt of cross-linking agent, in the uncured pre-gel, the method further comprising adding a composition comprising a trigger compound to the uncured pre-gel;
  C. a spray or coating of a solution of cross-linking agents, with the proviso that solid support is embedded in and/or placed on the uncured pre-gel before contacting the uncured pre-gel with the one or more cross linking agents.

In option A., in which the source of the cross-linking agent comprises a salt of the cross-linking agent, the method may further comprise adding an aqueous liquid, capable of dissolving the salt, to the uncured pre-gel and/or solid support.

In option B., the method further may also comprise adding an aqueous liquid, capable of dissolving the salt, but wherein the liquid may be added to the uncured pre-gel and/or composition comprising the trigger compound.

In some embodiments, the method further comprises one or more of the actions selected from a group comprising:

embedding a biocompatible solid support in the uncured pre-gel; placing the biocompatible solid support on the uncured pre-gel, and soaking said biocompatible solid support with said uncured pre-gel.

Said first surface may be for example tissue surface, synthetic graft surface, and/or organ surface.

Said application of adhesive may comprise sealing or closing an opening in the first surface.

In some embodiments the method further comprises sealing suture lines of end-to-side anastomosis of grafts, for example ePTFE grafts.

According to yet another aspect of the invention, use of a multicomponent adhesive is provided, wherein said treatment is selected from one or more of a group comprising end-to-side anastomosis of grafts, and sealing or closing an opening in a first surface selected from a group comprising tissue surface, synthetic graft surface, and organ surface.

In some embodiments the treatment further comprises treating the subject with one or more therapeutic material selected from one or more of a group comprising drugs, therapeutic proteins, growth factors, and hormones, wherein the multi component adhesive further comprises the one or more therapeutic materials.

For example, the use may be for the treatment of cancer or arrhythmia.

The treatment may further comprise making an adhesion barrier to a second surface,
wherein said second surface is selected from a group of tissue surface, synthetic graft surface, and organ surface.

It should be noted that the terms "adhesive" and "glue" are used hereinbelow in the same context to describe materials capable of adhering to surfaces. The particular term "sealant" is defined as materials capable of adhering to a surface while preventing fluid leaks from the surface. The term "adhesion-barrier" is used in the text to describe materials capable of reducing postoperative adhesions. Furthermore, the materials described in this invention may be also used as coatings, i.e. materials capable of adhering to a surface while forming a layer on it.

The term "curing" is defined as a process of cross-linking and hardening of a cross-linkable material, during which the material gains strength.

The term "cross-linking" is defined as forming bonds that link one polymer to other polymers. The bonds may be covalent bonds or physical bonds such as ionic bonds. The Polymers may be either synthetic polymers or natural polymers of mixtures thereof.

BRIEF DESCRIPTION OF THE FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments of the present invention only, and are presented in the cause of providing what is believed to be the most useful and readily understood description of the principles and conceptual aspects of embodiments of the invention. In this regard, no attempt is made to show structural details in more detail than is necessary for a fundamental understanding of the embodiments; the description taken with the drawings making apparent to those skilled in the art how the several forms of the invention may be embodied in practice. In the accompanying drawings.

DETAILED DESCRIPTION OF THE INVENTION

Figure 1:
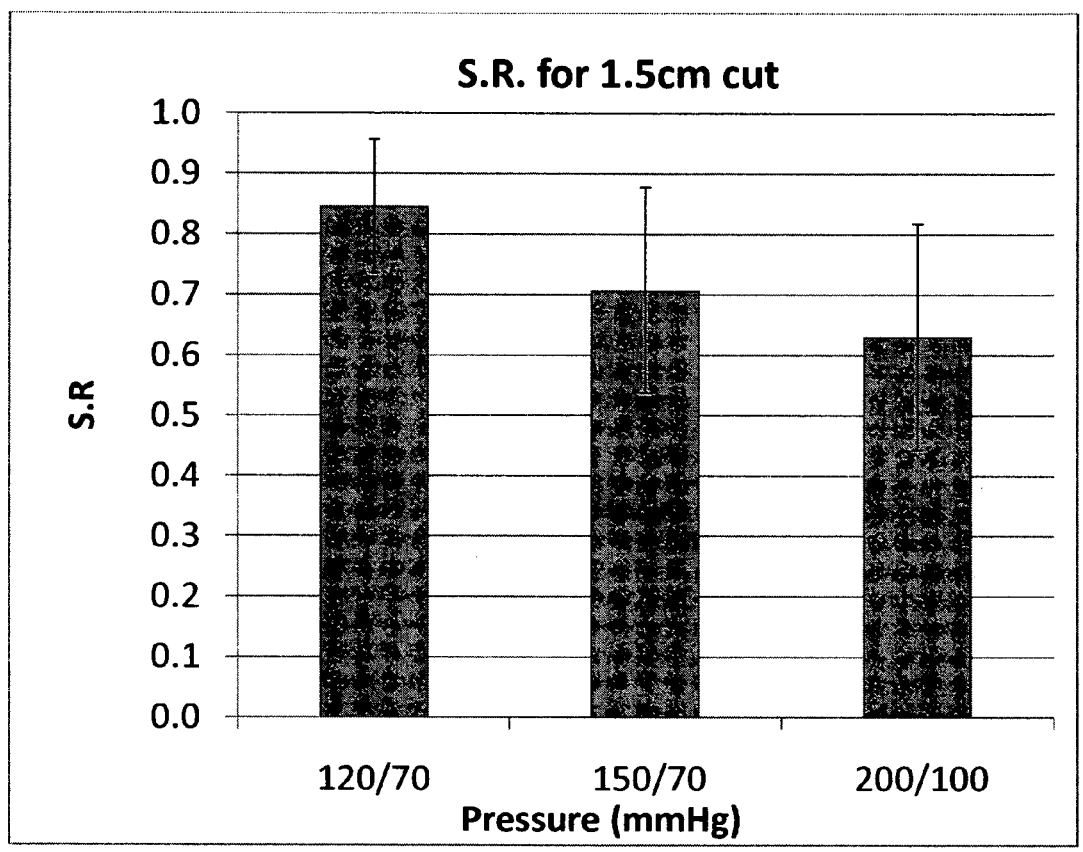
FIG. 1: shows S.R (sealing ratio) obtained by sealing incisions with the aid of an embodiment comprising a pre-gel and a cellulose patch containing a cross linking agent, evaluated using a flow system described below.

It is an object of the present invention to provide a composition of matter of a bioabsorbable surgical adhesive and a method of applying the same. The surgical adhesive may be adapted for internal use and be capable of adhering to wet as well as dry surfaces and tissues.

It is another object of the present invention to provide a method of producing a tissue adhesive that adheres to surfaces and may also become inert post curing so as to reduce or prevent unwanted adhesion such as post-surgical adhesions to adjacent tissue.

According to one aspect, a method of in situ application of a multi component adhesive to a subject is provided, the method comprising:
applying an uncured pre-gel to a first surface within the subject, the pre-gel comprising at least one water miscible cross-linkable polymer; subsequently contacting the uncured pre-gel with one or more cross linking agents; subsequently allowing the applied uncured pre-gel to cure and to become increasingly adhesive to the first surface during the curing.

The source of the cross linking agents may be either a solid support, or the uncured pre-gel itself, as will be described below.

However, it is stressed that when the uncured pre-gel is a source of cross-linking agents, the agents are necessarily bound in a water-insoluble inactive form, such that as long as there no reaction of inactive form that results in release of cross-linking agent, the gel remains uncured and thus may be essentially unadhesive due to lack of cohesive strength. In some embodiments a composition including a trigger compound may be added to the uncured pre-gel, the term "trigger" referring to the ability of the trigger compound to release a cross-linking agent from its insoluble form, such that the cross linking agent causes the uncured pregel to cure. As a result of gaining cohesive strength the composition resulting from the addition of trigger compound is strongly attached to the first surface.

While spraying cross-linking agent such as calcium ions on top of a water-soluble polymer such as alginate necessitates using relatively low ion concentrations, to prevent development of a "skin", leading to long curing times unless the alginate layer is very thin, by using triggers relatively homogeneous cured gels are obtained, which may be relatively strong.

It should be appreciated that a solid support is preferably integrated with the adhesive by adding it to the water soluble polymer prior to curing of the polymer, to provide additional mechanical strength to the adhesive. The solid support is preferably suitable for implantation e.g. application in a subject during surgery.

In some embodiments the water soluble polymers are polysaccharides, which can easily be cured in situ. For example, alginate ($C_6H_8O_6$) is a linear, water-soluble copolymer with homopolymeric blocks of α-L-guluronic acid (G) and its C-5 epimer β-D-mannuronic acid (M) residues, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks.

Cross linking (gelation) of alginates is based on their affinity toward certain multivalent cations and their ability to bind those ions selectively and cooperatively, a process which leads to the formation of ionically cross linked alginate gels. Examples to alginate types used are Protanal LF 200 S (FMC Biopolymers) with G content of ~70% and Protanal HF 120 RBS with G content of ~50% (FMC Biopolymers).

According to one aspect a surgical multi component adhesive especially suitable for internal use in a subject is provided. The adhesive may be bioabsorbable.

According to one embodiment, a multi component adhesive is provided that comprises:
1. An uncured pre-gel including a solution of cross-linkable polysaccharide, such as alginate. The pre-gel may be lightly cross-linked, yet it is still substantially fluid and easily administrable to a surface.
2. A solid carrier incorporating a cross linking agent or a soluble salt of the agent. The solid carrier can be a mesh or can optionally be a patch of fibrous structure. For example the solid carrier can be made of either oxidized regenerated cellulose, dry hydrophilic water-soluble polymer such as polyethylene glycol, polyvinyl alcohol, alginate or dextran;

The cross linking agent is capable of cross linking the polysaccharide upon contact of the solid carrier incorporating the cross linking agent with the polysaccharide, thus providing a cured gel. For example, the cross linking agent can be calcium or another multivalent ion. The cross linking agent is incorporated within the solid carrier, and is released from it to the pre-gel. During the curing process, the polysaccharide adheres to the surface. The solid carrier may additionally provide mechanical support to the gel, or enhance its properties in other ways.

According to a second embodiment, the dual component adhesive comprises:
1. A dry uncured pre-gel including a dehydrated solution of cross-linkable polysaccharide, such as alginate. 2. A solid carrier of a cross linking agent or a soluble salt of the agent. The solid carrier can be a mesh or can optionally be a patch of fibrous structure.

For example the solid carrier can be made of either oxidized regenerated cellulose, dry hydrophilic water-soluble polymer such as polyethylene glycol, polyvinyl alcohol, alginate or dextran.

In embodiments in which the solid carrier incorporates the agent in water-soluble salt form, the solid carrier itself is typically provided dry—in which case an aqueous solution may be added at a desired time to the solid carrier. Alternatively, the aqueous solution may be added to the polymer. In either case, the aqueous solution is capable of both dissolving the salt and dissolving the polymer.

The cross linking agent is capable of cross linking the polysaccharide upon contact of the solid carrier incorporating the cross linking agent with the polysaccharide, thus providing a cured gel. For example, the cross linking agent can be calcium or other multivalent ions. The cross linking agent is incorporated within the solid carrier, and is released from it to the pre-gel. During the curing process, the polysaccharide cures and adheres to the surface with increasing adhesion strength. The solid carrier may additionally provide mechanical support to the gel, or enhance its properties in other ways.

According to a third embodiment, dual component adhesive for preparation of an adhesive is provided that comprises:
A pre-gel made of a cross-linkable polysaccharide, such as alginate, and multivalent ions provided in an inactive form, i.e. are essentially incapable of cross-linking the polysaccharide prior to application, and are activated upon contact with a trigger compound. After contact with the trigger compound, the cross linking agent becomes active, i.e. capable of cross linking the polysaccharide, thus providing a cured gel. During the curing process, the polysaccharide increasingly adheres to the surface.

Optionally, colorant or other components for controlling physical/chemical properties of the pre-gel (salts, preservatives, etc.) can be provided to any of the components of the adhesive.

Optionally, pharmaceutical substances such as drugs, antioxidants, growth factors, therapeutic proteins/peptides or other therapeutic molecules for wound healing, anti-cancer, anti-arrhythmia or for other purposes are incorporated within the liquid or the solid carrier so as to be released in the area to be treated.

It is emphasized that the solid carrier is preferably bioabsorbable.

It will occur that by embedding, mixing, blending or even laying a carrier on top of a layer of polysaccharide on a surface such as an organ in a subject, the carrier itself becomes attached to the pre-gel.

Some embodiments are suitable for manufacture of adhesives capable of being used as sealants for preventing fluid leaks from internal tissues or organs as well as from synthetic grafts/implants.

The above described multi component adhesives and the adhesives made thereof may be capable of being used for local delivery of drugs or other therapeutic materials into tissues.

Application Methods

Several methods are used to apply adhesive in the site that requires tissue repair or tissue sealing.
  (1) A layer of a liquid pre-gel is spread on the surface and the solid carrier is embedded in it either manually or using a designed applicator. The composition is allowed to cure.
  (2) A layer of a dry pre-gel is placed on the surface and the solid carrier is placed on top of it either manually or using a designed applicator. The composition is allowed to cure. Optionally addition of liquids, such as saline, may be provided.
  (3) A dry pre-gel pre-combined with the solid carrier is placed on the surface. The composition is allowed to cure. Optionally addition of liquids, such as saline, may be provided.
  (4) A dry pre-gel is placed on the surface. Optionally addition of liquids, such as saline, may be provided.
  (5) A liquid pre-gel containing an inactive form of a cross linking agent, for example insoluble salt of multivalent ions (e.g. $CaCO_3$ or CaEGTA) is mixed with a trigger compound such as slowly hydrolyzing D-gluco-d-lactone (GDL, The mixture is spread on the surface. The composition hardens with time due to the slow dissolution of the multivalent salt.

(6) A dry pre-gel containing an inactive form of a cross linking agent, for example, insoluble salt of multivalent ions (e.g. $CaCO_3$ or CaEGTA) and a trigger compound solution (e.g. of the slowly hydrolyzing D-gluco-d-lactone (GDL)) is placed on the surface. The composition hardens with time due to the hydration and dissolution of the multivalent salt.

(7) Options (5) and (6) may optionally be used in combination with a solid support such as is used for the solid carriers.

In all the above cited examples, once the pre-gel is cured, it loses its adherence capability thus acts as a barrier that may prevent post-surgical adhesion.

Sealing Capabilities

Sealing capabilities are evaluated in vitro using a pulsating flow system. The system is composed of computer, controller, pump, pressure transducer and solenoid valves. As a model to human artery, a pig aorta is chosen. In experiments made in the system, each aorta was connected to the system by plastic connectors. Punctures were made in the aorta in order to simulate a leak. Different leaks were simulated either by simply puncturing the aorta with 20 mm 0.5 cc surgical needle (six holes), a stitched diagonal incision in the length of 10 mm stitched by Prolene thread (4-0, 20 mm 0.5 cc needle, 2 mm between stitches) and finally an unstitched incision of 10 mm.

Each leak was characterized for flow rate before and after the application of the sealant. Different pressures were also tested ranging from 70/120 mmHg up to 70/350 mmHg. In order to get proper statistics each experiment was repeated six times or more.

Example 1

Sealing capability of the above-described sealant was evaluated using the described flow system. A 1.5 cm incision was sutured with a surgical thread and needle, and then an alginate-based solution (25-45 mg/ml) was applied by placing a calcium-containing regenerated cellulose patch. The flow rate through the suture line before and after sealant application ($Q_0$ and $Q_f$, respectively) was measured. A sealing ratio was defined as Sealing ratio=$1-Q_f/Q_0$, e.g. sealing ratio of 1 represents complete sealing. Sealing ratios of up to 0.85 were achieved as can be seen, for example, in FIG. 1.

Example 2

Sealing capability of alginate cured in-situ with the aid of oxidized regenerated cellulose patch was evaluated using the described flow system. A 1.5 cm incision was sutured with a surgical thread and needle, alginate solution (35 mg/ml) was applied and cured by placing a regenerated cellulose patch which was pre-soaked with $CaCl_2$ solution and dried prior to its use. The flow rate through the suture line before and after glue application ($Q_0$ and $Q_f$, respectively) was measured. Sealing ratio of 0.85 was achieved as can be seen in FIG. 1.

FIG. 1 depicts S.R obtained by sealing incisions with the above described composition [n=6]

Example 3

Sealing capability of the above-described sealant was evaluated using the described flow system.

A 6 mm PTFE graft was evaluated using the described flow system.

A 6 mm PTFE graft was stitched end-to-side to a 10 mm hole longitudinal incision in the artery with surgical thread and needle.

An alginate-based solution (25-45 mg/ml alginate) was applied and cured by placing a calcium-containing regenerated cellulose patch.

The flow rate through the suture line before and after sealant application ($Q_0$ and $Q_f$, respectively) was measured.

Sealing ratio of up to 0.62 was measured. Sealing ratio of up to 0.62 was achieved as can be seen, for example, in FIG. 3.

Figure 2:
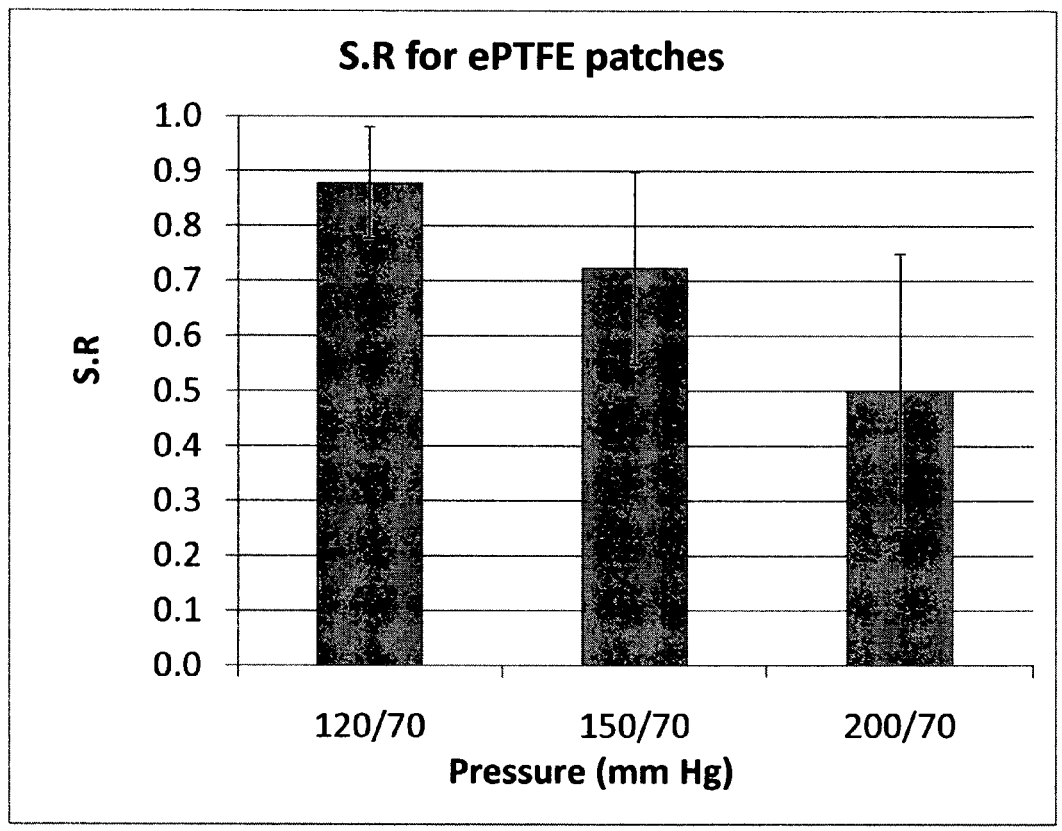
FIG. 2: shows S.R obtained by sealing suture lines of ePTFE patches stitched to blood vessels, with a similar embodiment, evaluated using the described flow system.

FIG. 2 is a S.R obtained by sealing stitched ePTFE patches, using the above described composition [n=6].

Example 4

Sealing capability of alginate cured in-situ with the aid of oxidized regenerated cellulose patch was evaluated using the described flow system.

A 6 mm PTFE graft was stitched to a 10 mm longitudinal cut in the artery (end to side) with surgical thread and needle.

Alginate solution (35 mg/ml) was applied and cured by placing a regenerated cellulose patch which was pre-soaked with $CaCl_2$ solution and dried prior to its use.

The flow rate through the suture line before and after glue application ($Q_0$ and $Q_f$, respectively) was measured. Sealing ratio of 0.62 was achieved as can be seen in FIG. 3.

Figure 3:
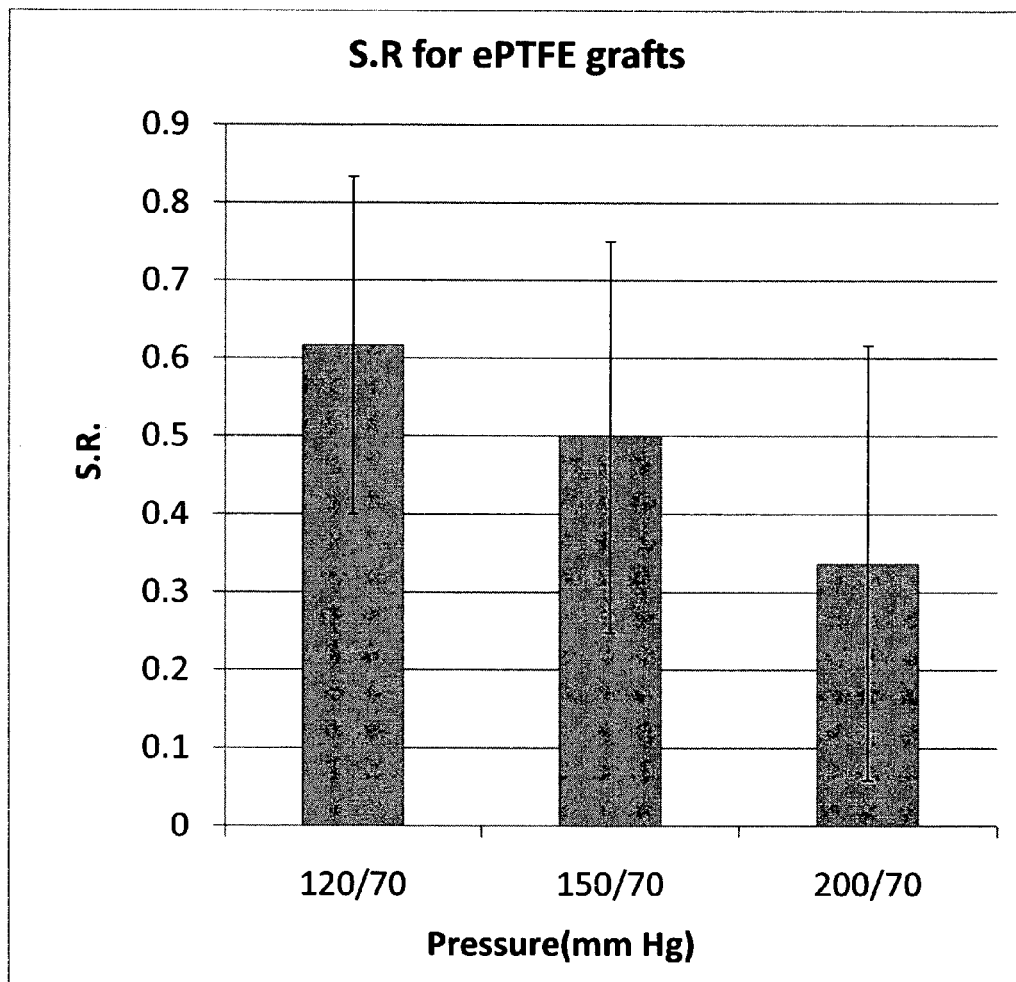
FIG. 3: shows a S.R obtained by sealing suture lines of end-to-side anastomosis of ePTFE grafts to bovine aorta ex-vivo, with a similar embodiment, evaluated using the described flow system.

FIG. 3 shows a S.R obtained by sealing end-to-side anastomosis of ePTFE grafts to bovine aorta ex-vivo with the above described composition [n=6].

Example 5

Sealing capability of the above described sealant was evaluated in-vivo on pigs' carotid and femoral arteries. Two surgical procedures were used:
1) 8-10 mm arteriotomy, stitched with two separate stitches
2) end-to-side anastomosis with ePTFE graft, attached to the artery by continuous suturing.

Animals were heparinized, and blood flow through the stitches prior to application of the sealant was intense.

Two trials were conducted on each surgical model. The sealant was able to achieve 100% sealing immediately after resuming blood flow to the vessel, in all four experiments.

Example 6

The performance of adhesives comprising a pre-gel comprising alginate solution 35-40 mg/mL and a solid carrier of a cross linking agent (a solution of calcium chloride in oxidized regenerated cellulose) was studied by testing its ability to seal blood leakage from porcine carotid and femoral arteries. Two surgical procedures were used in-vivo: 1) 8-10 mm arteriotomy (artery incision), stitched with two interrupted stitches 2) end-to-side anastomosis with ePTFE graft, attached to the artery by continuous suturing.

Animals were heparinized, and bleeding through the stitches prior to application of the sealant was from moderate to severe.

The adhesive was applied on the suture line of either of the above mentioned procedures, and allowed to cure. The adhesive was able to achieve 100% sealing at less than 1 minute after resuming blood flow to the vessel, in all experiments.

Figure 4:
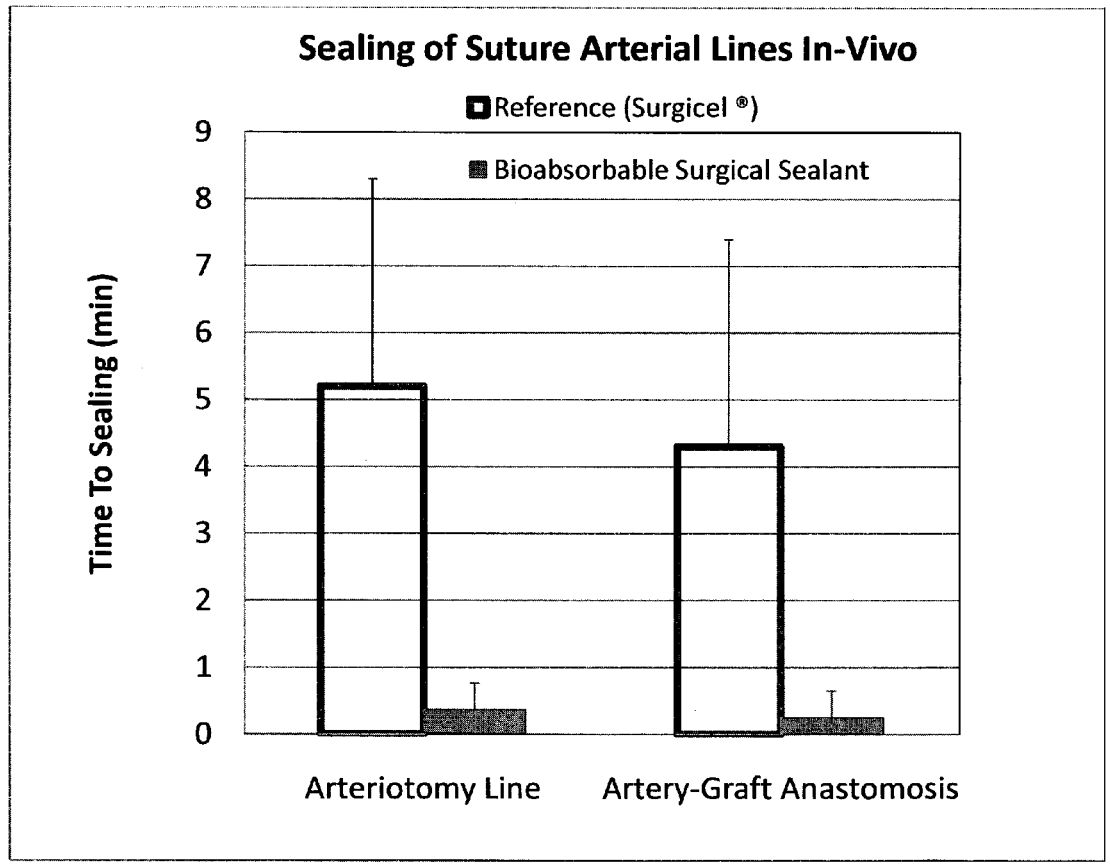
FIG. 4 depicts a graph of time to sealing, determined as the time of bleeding cessation in minutes from the time of de-clamping and circulation is restored until bleeding is stopped, obtained by in-vivo sealing both arteriotomies stitched by two interrupted sutures with a similar embodiment and gold standard treatment; and end-to-side anastomoses of ePTFE grafts to porcine carotid and femoral arteries with the embodiment and the gold standard treatment.

Sealing capability in-vivo can is demonstrated in FIG. 4, in which the time to sealing is determined as the time of bleeding cessation in minutes from the time of de-clamping and circulation is restored until bleeding is stopped, obtained by in-vivo sealing both arteriotomies stitched by two interrupted sutures with an embodiment [n=4] and gold standard treatment [n=5]; and end-to-side anastomoses of ePTFE grafts to porcine carotid and femoral arteries with the embodiment [n=8] and gold standard treatment [n=7].

Example 7

The adhesive described in Example 6 was tested. The adhesive resorbs in the body tissue within a few weeks after the application. As demonstrated in seven pigs tested at week 4 post-application, none to minimal residual amounts of the above described composition were found in five individuals, and moderate residual amounts of the above described composition were observed in two individuals. Presence of the above described composition in the tissue did not result in any abnormal tissue reaction and did not interfere with normal function of the tissues and organs.

The examples described above present various selected embodiments of a multi component adhesive for preparation of adhesives and methods of preparation of the adhesives. It is noted that further embodiments are anticipated which also fall within the scope of the present invention. The scope of the present invention is defined by the claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A multi component adhesive comprising:
   a) uncured pre-gel that comprises
      (i) at least one water miscible cross-linkable polymer selected from the group consisting of naturally existing form of a carbohydrate, a synthetically prepared form of carbohydrate and a salt of a polysaccharide, and (ii) at least one water-insoluble salt of a cross linking agent; and
   b) a composition comprising at least one trigger compound capable of triggering dissolution of the salt of the cross linking agent into the pre-gel, wherein the uncured pre-gel applied to a first surface is capable of curing and increasingly adhering to the surface after adding the composition comprising the trigger compound to the uncured pre-gel.

2. The multi component adhesive of claim 1, wherein an aqueous liquid capable of dissolving the salt of the cross linking agent is further added to the uncured pre-gel and/or the said composition.

3. The multi component adhesive of claim 1, wherein both the pre-gel and the composition are dry, wherein curing and adhering to the first surface occurs upon adding an aqueous liquid capable of dissolving the salt to the uncured pre-gel and/or said composition.

4. The multi component adhesive of claim 1, further comprising a biocompatible solid support.

5. The multi component adhesive of claim 4, wherein the biocompatible solid support is bioabsorbable.

6. The multi component adhesive of claim 5, wherein the solid support is one or more materials selected from one or more of the group consisting of: poly(a-caprolactone) (PCL), poly(glycolide) (PGA), poly(lactide) (PLA), and poly(glycolide-co-lactide) (PLGA), and oxidized regenerated cellulose, and hydrophilic water-soluble polymer, selected from one or more of the group comprising: alginate, polyethylene glycol, polyvinyl alcohol, dextran, and pectin.

7. The multi component adhesive of claim 4, wherein the solid support comprises a mesh.

8. The multi component adhesive of claim 7, wherein the mesh comprises a fibrous structure.

9. The multi component adhesive of claim 1, wherein said pre-gel further comprising non-soluble suspended solids.

10. The multi component adhesive as claimed in claim 9, wherein said suspended solids are in the form of particles comprising fibers.

11. The multi component adhesive as claimed in claim 1, wherein said at least one cross linking agent comprises multivalent charged materials made from dissolution of one or more of a group comprising polyelectrolytes, organic salts, and inorganic salts.

12. The multi component adhesive as claimed in claim 1, further comprising one or more therapeutic materials selected from one or more of a group comprising drugs, therapeutic proteins, growth factors, and hormones.

13. The multi component adhesive of claim 1, wherein the cured pre-gel is capable of being an adhesion barrier to a second surface, wherein said second surface is selected from a group of tissue surface, synthetic graft surface, and organ surface.

14. Method of treatment of a subject comprising: a) providing uncured pre-gel that comprises (i) at least one water miscible cross-linkable polymer selected from the group comprising naturally existing form of a carbohydrate, a synthetically prepared form of carbohydrate and a salt of a polysaccharide, and (ii) at least one water-insoluble salt of a cross linking agent;
   b) providing a composition comprising at least one trigger compound capable of triggering dissolution of the salt of the cross linking agent into the pre-gel;
   c) applying the uncured pre-gel to a first surface on or within the subject; subsequently contacting the uncured pre-gel with the composition comprising at least one trigger compound;
   d) subsequently allowing the applied uncured pre-gel to cure and increasingly adhere to the first surface.

15. The treatment of claim 14 further comprising adding an aqueous liquid, capable of dissolving the salt, to the uncured pre-gel and/or the composition.

16. The treatment of claim 14, further comprising one or more of the actions selected from a group comprising: embedding a biocompatible solid support in the uncured pre-gel; placing the biocompatible solid support on the uncured pre-gel, and soaking said biocompatible solid support with said uncured pre-gel.

17. The treatment of claim 16, wherein the biocompatible solid support is bioabsorbable.

18. The treatment as claimed in claim 16, wherein said solid support is coated with said cross linking agent.

19. The treatment as claimed in claim 14, wherein said first surface is selected from a group comprising tissue surface, synthetic graft surface, and organ surface.

20. The treatment as claimed in claim 14, wherein said application of adhesive comprises sealing or closing an opening in the first surface.

21. The treatment as claimed in claim 14, the treatment further comprising sealing suture lines of end-to-side anastomosis of grafts.

22. The multi component adhesive of claim 1 wherein said uncured pre-gel consists of
   (i) a water miscible cross-linkable polymer selected from the group consisting of naturally existing form of a carbohydrate, a synthetically prepared form of carbohydrate and a salt of a polysaccharide, and
   (ii) at least one water-insoluble salt of a cross linking agent.

* * * * *